(12) United States Patent
Sun et al.

(10) Patent No.: US 11,311,651 B2
(45) Date of Patent: Apr. 26, 2022

(54) ABSORBABLE BIOMEDICAL COMPOSITE MATERIAL AND PREPARATION METHOD THEREFOR

(71) Applicant: SHENZHEN CORLIBER SCIENTIFIC Co., Ltd., Shenzhen (CN)

(72) Inventors: Yang Sun, Shenzhen (CN); Feng Pan, Shenzhen (CN); Yucheng Huang, Shenzhen (CN); Dong Xiang, Shenzhen (CN)

(73) Assignee: SHENZHEN CORLIBER SCIENTIFIC CO., LTD., Shenzhen (CN)

( * ) Notice: Subject to any disclaimer, the term of this patent is extended or adjusted under 35 U.S.C. 154(b) by 0 days.

(21) Appl. No.: 16/615,133

(22) PCT Filed: Jul. 15, 2018

(86) PCT No.: PCT/CN2018/095731
§ 371 (c)(1),
(2) Date: Nov. 20, 2019

(87) PCT Pub. No.: WO2019/015542
PCT Pub. Date: Jan. 24, 2019

(65) Prior Publication Data
US 2020/0171207 A1 Jun. 4, 2020

(30) Foreign Application Priority Data

Jul. 15, 2017 (CN) .......................... 201710578058.8
Jul. 15, 2017 (CN) .......................... 201710578059.2

(51) Int. Cl.
*A61L 27/46* (2006.01)
*A61L 27/48* (2006.01)
*A61L 27/58* (2006.01)

(52) U.S. Cl.
CPC ............... *A61L 27/46* (2013.01); *A61L 27/48* (2013.01); *A61L 27/58* (2013.01)

(58) Field of Classification Search
CPC .......... A61L 27/46; A61L 27/58; A61L 27/48; C08L 67/04
See application file for complete search history.

(56) References Cited

U.S. PATENT DOCUMENTS

2013/0280335 A1* 10/2013 Han ...................... A61L 31/128
424/497

FOREIGN PATENT DOCUMENTS

CN 1544524 * 11/2004
CN 105419395 * 3/2016

* cited by examiner

*Primary Examiner* — Jianfeng Song
(74) *Attorney, Agent, or Firm* — Avek IP, LLC

(57) ABSTRACT

Provided are an absorbable biomedical composite material and a preparation method therefor. The absorbable biomedical composite material comprises: substrate granules containing a calcium-phosphorus compound; an intermediate layer which is coated on the surface of each of the substrate granules and has a first glass transition temperature, the first glass transition temperature being not higher than normal human body temperature; and a polymer matrix which is formed on the outer surface of the intermediate layer and has a second glass transition temperature, the second glass transition being higher than the first glass transition temperature. The absorbable biomedical composite material has increased mechanical strength and also improved toughness.

3 Claims, 6 Drawing Sheets

ABSORBABLE BIOMEDICAL COMPOSITE MATERIAL AND PREPARATION METHOD THEREFOR

TECHNICAL FIELD

The present disclosure is related to biomedical composite materials, and more particularly to an absorbable biomedical composite material and a preparation method therefor.

BACKGROUND

The human bones contain water, organic substances (bone glue), inorganic salts and etc. Calcium-phosphorus compounds are the main inorganic salts and distributed in the organic substances in the forms of crystalline hydroxyapatites and amorphous calcium phosphates. Therefore, inorganic salts containing calcium-phosphorus compounds, especially hydroxyapatites, calcium phosphates and the like, are similar to the inorganic salts in human bones and excellent in biocompatibility and bioactivity. Biodegradable polyester materials, such as polylactic acid, polycaprolactone, polyglycolide and etc., having good biodegradability, biocompatibility and mechanical properties, are common absorbable medical polymer materials and widely used in the medical field. A composite material prepared by calcium-phosphorus-containing inorganic salts with an absorbable polyester material may take advantage of both materials, providing good biocompatibility, bioactivity and mechanical properties when used in bone fixation and bone repair.

However, most calcium-phosphorus-containing inorganic salts are hydrophilic and hardly compatible with absorbable polyester materials. When the two are blended, there is no sound interfacial force, resulting in aggregation of inorganic salts and their uneven distribution in the polyester matrix. Accordingly, the stress is usually concentrated, and cracks occur at the interfaces due to peeling of the matrix from the fillers, which badly influences the composite materials' mechanical properties. Further, the addition of inorganic salt granules usually deteriorates the polyester material's toughness, making the composite material easy to break, which restricts its application in bone orthopedics. Thus, orthopedic medical materials made of ordinary polyesters and calcium-phosphorus-containing inorganic composite materials may bring huge risk to patients in clinical uses.

To solve the above problems, Patent Document 1 proposes a hydroxyapatite/polylactic acid composite material. In that material, hydroxyapatite is modified through adsorbing low molecular weight polylactic acids on its surface. However, although the binding capacity of the modified hydroxyapatite to the polylactic acid matrix is enhanced, there still lacks a strong interfacial force, and therefore the mechanical properties of the resulting composite material need to be improved.

In addition, Patent Document 2 also proposes a hydroxyapatite/polylactic acid composite material, which is prepared through in situ polymerization of hydroxyapatites and polylactic acids. There are covalent bonds between hydroxyapatites and polylactic acids, which helps to improve distribution of hydroxyapatites in the polylactic acids and to enhance the interfacial force, providing better the mechanical properties. However, since there is no buffer between the rigid hydroxyapatite granules and the polylactic acids, the toughness of the composite material may be seriously deteriorated, and thus brittle fracture is prone to occur, which is disadvantageous in the application of the composite material in orthopedic clinics.

Further, several composite fibers are adopted in Patent Document 3 to reinforce poly(DL-lactic acid), wherein the composite fibers comprise calcium polyphosphate and hydroxyapatite, calcium carbonate or zirconium oxide. The obtained composite material has its strength improved. However, the strength improvement is not significant, as there is no strong interfacial force between the composite fibers and poly(DL-lactic acid), which also leads to deteriorated toughness of the composite material.

PRIOR ART DOCUMENTS

Patent Documents

Patent Document 1: Chinese Patent CN102153058B
Patent Document 2: Chinese Patent CN103319696A
Patent Document 3: Chinese Published Patent Application CN1537892A

SUMMARY OF THE INVENTION

The present disclosure is implemented in view of the above-described prior arts, and aims to provide an absorbable biomedical composite material with increased mechanical strength and improved toughness.

Therefore, the present disclosure, in a first aspect, provides an absorbable biomedical composite material comprising: substrate granules containing a calcium-phosphorus compound; an intermediate layer coated on the surface of each substrate granule and having a first glass transition temperature, the first glass transition temperature being not higher than normal human body temperature; and a polymer matrix formed on the outer surface of the intermediate layer and having a second glass transition temperature, the second glass transition being higher than the first glass transition temperature.

In the first aspect of the present disclosure, the intermediate layer is formed between the substrate granule and the polymer matrix, and the glass transition temperature of the intermediate layer is not higher than normal human body temperature. Therefore, when the composite material of the present disclosure is applied to clinical orthopedics, the intermediate layer maintains in the rubbery state (highly elastic state) inside the human body, and the rubbery intermediate layer may release the concentrated stress caused by the substrate granules and reduce microcracks, thereby improving the toughness of the composite material. In addition, the substrate granules may suppress the severe deformation of the rubbery intermediate layer under a certain stress, thereby inhibiting the decrease of the composite material in the strength caused by the addition of the rubbery intermediate layer material.

Further, in the composite material according to the first aspect of the present disclosure, the substrate granules may optionally contain one or more selected from the group consisting of hydroxyapatite, calcium polyphosphate, and tricalcium phosphate. In this case, the constituents of the substrate granules are similar to those of human bones, such that the bioactivity and biocompatibility of the composite material can be improved.

Further, in the composite material according to the first aspect of the present disclosure, the substrate granules may be optionally rigid. Therefore, the mechanical strength of the composite material can be improved.

Further, in the composite material according to the first aspect of the present disclosure, optionally, the intermediate layer is a polymer layer, and the substrate granules are covalently bonded to the intermediate layer. Thus, a strong interfacial force can be formed between the substrate granules and the intermediate layer, thereby effectively improving the bonding force therebetween and facilitating the force transfer.

Further, optionally, the substrate granules account for 1 wt % to 10 wt %, and the intermediate layer accounts for 1 wt % to 10 wt % of the composite material according to the first aspect of the present disclosure. In this case, the mechanical strength of the composite material can be improved while other properties such as the toughness of the composite material are not affected or less affected.

Further, in the composite material according to the first aspect of the present disclosure, optionally, the polymer matrix is formed on the intermediate layer in an in situ polymerization manner. In this case, a strong interfacial force such as covalent bonds can be formed between the intermediate layer and the polymer matrix, thereby improving the bonding force therebetween and facilitating the force transfer.

Further, in the composite material according to the first aspect of the present disclosure, optionally, the intermediate layer contains a homopolymer of p-dioxanone or caprolactone, or a random copolymer or a block copolymer of two or more selected from the group consisting of lactide, caprolactone, p-dioxanone, and glycolide. In this case, the intermediate layer is formed to be absorbable, facilitating the application of the composite material in the field of bone orthopedics, especially as absorbable bone orthopedic materials.

Further, in the composite material according to the first aspect of the present disclosure, optionally, the intermediate layer is covalently bonded to the polymer matrix. In this case, a strong interfacial force may be formed between the intermediate layer and the polymer matrix, thereby improving the bonding force therebetween and facilitating the force transfer.

In a second aspect, the present disclosure provides a method for preparing an absorbable biomedical composite material, comprising steps of preparing substrate granules composed of a calcium-phosphorus compound; sufficiently mixing the substrate granules with a first reactant monomer to obtain a mixture; adding a catalyst to the mixture, heating the mixture to 80° C. to 180° C. in the presence of an inert gas, and allowing the mixture to react for 2 to 48 hours, such that an intermediate layer composed of the first reactant monomer is coated on each substrate granule; and adding a second reactant monomer, keeping heating, and allowing the resultant mixture to react for another 2 to 48 hours to form a polymer matrix on the intermediate layer. In this case, a composite material containing an intermediate layer can be formed with improved mechanical strength and toughness, which is of great significance in the application of orthopedic medical materials.

Further, in the preparation method according to the second aspect of the present disclosure, optionally, the first reactant monomer and the second reactant monomer are independently at least one selected from the group consisting of lactide, caprolactone, p-dioxanone, and glycolide. In this case, an absorbable intermediate layer and an absorbable polymer matrix can be prepared to facilitate the application of the composite material in the field of orthopedics, especially in the field of absorbable orthopedic materials.

Further, in the preparation method according to the second aspect of the present disclosure, optionally, the first reactant monomer is different from the second reactant monomer. In this case, the glass transition temperature of the intermediate layer or the polymer matrix can be controlled by adjusting the monomer type, monomer's mass or ratio, and etc., to facilitate the application of the composite material in the field of orthopedics.

According to the first and second aspects of the present disclosure, an absorbable biomedical composite material having high mechanical strength and good toughness is provided as well as its preparation method.

In a third aspect, the present disclosure provides an absorbable biomedical polylactic acid composite material comprising: core-shell structures, each includes a substrate granule containing a calcium-phosphorus compound, an intermediate layer coated on the surface of the substrate granule, and a polymer layer formed on the outer surface of the intermediate layer; and a polylactic acid matrix which forms a stereocomplex with the polymer layer and has a third glass transition temperature, wherein the intermediate layer has a fourth glass transition temperature which is not higher than normal human body temperature, and the third glass transition temperature is higher than the fourth glass transition temperature.

In the third aspect of the present disclosure, the absorbable biomedical polylactic acid composite material comprises the core-shell structures and the polylactic acid matrix, wherein the polylactic acid matrix forms a stereocomplex force with each core-shell structure. The stereocomplex force facilitates the force transfer between the polylactic acid matrix and the core-shell structure and assists in the dispersion of the core-shell structures in the polylactic acid matrix. In the core-shell structure, the intermediate layer exists between the substrate granule and the polymer layer, and the glass transition temperature of the intermediate layer is not higher than normal human body temperature, which keeps the intermediate layer of the core-shell structure in a rubbery state (highly elastic state) inside the human body when the composite material of the present disclosure is applied to clinical orthopedic treatment, wherein the rubbery intermediate layer can alleviate the stress concentration and microcracks caused by the substrate granules, thereby improving the toughness of the composite material. Meanwhile, the substrate granules can fix the severe deformation of the rubbery intermediate layer under a certain stress, thereby preventing the strength of the composite material from decreasing.

Further, in the polylactic acid composite material according to the third aspect of the present disclosure, optionally, the substrate granules contain one or more selected from the group consisting of hydroxyapatite, calcium polyphosphate, and tricalcium phosphate. In this case, since the constituents of the substrate granules are similar to those of human bones, the polylactic acid composite material has improved bioactivity and biocompatibility.

Further, in the polylactic acid composite material according to the third aspect of the present disclosure, optionally, the substrate granules are rigid. Therefore, the mechanical strength of the polylactic acid composite material can be improved.

Further, optionally, the substrate granules account for 1 wt % to 30 wt % of the the polylactic acid composite material according to the third aspect of the present disclosure. In this case, the mechanical strength of the polylactic acid composite material will be improved, and meanwhile other properties such as the toughness of the polylactic acid composite material may not be affected or less affected.

Further, in the polylactic acid composite material according to the third aspect of the present disclosure, optionally, an average granule size of the substrate granules ranges from 5 nm to 200 μm. In this case, the mechanical strength of the polylactic acid composite material may be improved, and the toughness of the polylactic acid composite material may not be affected or less affected.

Further, in the polylactic acid composite material according to the third aspect of the present disclosure, optionally, the intermediate layer contains a homopolymer of p-dioxanone or caprolactone, or a random copolymer or a block copolymer of two or more selected from the group consisting of lactide, caprolactone, p-dioxanone, and glycolide. In this case, the intermediate layer is formed as an absorbable polymer material, which facilitates the application of the composite material in the field of orthopedics, especially in the field of absorbable orthopedic materials.

Further, in the polylactic acid composite material according to the third aspect of the present disclosure, optionally, the intermediate layer is composed of a polymer material, and the substrate granules are covalently bonded to the intermediate layer. In this case, a strong interfacial force can be formed between the substrate granules and the intermediate layer, thereby improving the bonding force therebetween and facilitating the force transfer.

Further, in the polylactic acid composite material according to the third aspect of the present disclosure, optionally, the polymer layer contains a homopolymer of a first type of lactide, or a random copolymer or a block copolymer of the first type of lactide with one or more monomers selected from the group consisting of a second type of lactide, caprolactone, p-dioxanone, and glycolide; and the polylactic acid matrix contains a homopolymer of the second type of lactide, or a random copolymer or block copolymer of the second type of lactide with one or more monomers selected from the group consisting of the first type of lactide, caprolactone, p-dioxanone, and glycolide; wherein one of the first type of lactide and the second type of lactide is L-lactide, and the other is D-lactide. In this case, the polymer layer and the polylactic acid matrix may be composed of L-polylactic acid and D-polylactic acid, or alternatively D-polylactic and L-polylactic acid, respectively. When the two are put together, special hydrogen bonds (also referred to as stereocomplex force) are formed, which are more stable than common hydrogen bonds, and accordingly a stereocomplex is generated, providing good interfacial force and stability.

Further, in the polylactic acid composite material according to the third aspect of the present disclosure, optionally, the crystallization ratio of the stereocomplex is 1% to 40%. In this case, the mechanical properties of the polylactic acid composite material may be effectively improved.

In a fourth aspect, the present disclosure provides a method for preparing an absorbable biomedical polylactic acid composite material, comprising the steps of preparing substrate granules containing a calcium-phosphorus compound; sufficiently mixing the substrate granules with a third reactant monomer to obtain a mixture; adding a catalyst to the mixture, and heating the mixture to 80° C. to 180° C. in the presence of an inert gas, and allowing the mixture to react for 2 to 48 hours, such that an intermediate layer composed of the third reactant monomer is coated on each substrate granule; adding a fourth reactant monomer, keeping heating, and allowing the resultant mixture to react for another 2 to 48 hours to form a polymer layer on the intermediate layer, thereby obtaining core-shell structures; and blending the core-shell structures and a polylactic acid matrix in a prescribed ratio to obtain a stereocomplex formed by the core-shell structures and the polylactic acid matrix. In this case, a polylactic acid composite material may be formed to contain the core-shell structures and the polylactic acid matrix with enhanced mechanical strength and toughness, which is of great significance in the application of orthopedic medical materials.

Further, in the preparation method according to the fourth aspect of the present disclosure, optionally, the polymer layer contains a homopolymer of a first type of lactide, or a random copolymer or block copolymer of the first type of lactide with one or more monomers selected from the group consisting of a second type of lactide, caprolactone, p-dioxanone, and glycolide; and the polylactic acid matrix contains a homopolymer of the second type of lactide, or a random copolymer or a block copolymer of the second type of lactide with one or more monomers selected from the group consisting of the first type of lactide, caprolactone, p-dioxanone, and glycolide; wherein one of the first type of lactide and the second type of lactide is L-lactide, and the other is D-lactide. In this case, the polymer layer and the polylactic acid matrix may be composed of L-polylactic acid and D-polylactic acid, or alternatively D-polylactic acid and L-polylactic acid, respectively. When the two are put together, special hydrogen bonds (also referred to as stereocomplex force) are formed, which are more stable than common hydrogen bonds, and accordingly a stereocomplex is generated, providing good interfacial force and stability.

Further, in the preparation method according to the fourth aspect of the present disclosure, optionally, the intermediate layer is composed of a polymer material, and the substrate granules are covalently bonded to the intermediate layer. In this case, a strong interfacial force can be formed between the substrate granules and the intermediate layer, thereby facilitating the force transfer.

According to the third and fourth aspects of the present disclosure, an absorbable biomedical composite material having high mechanical strength and good toughness is provided as well as its preparation method.

REFERENCE NUMERALS

Figure 1:
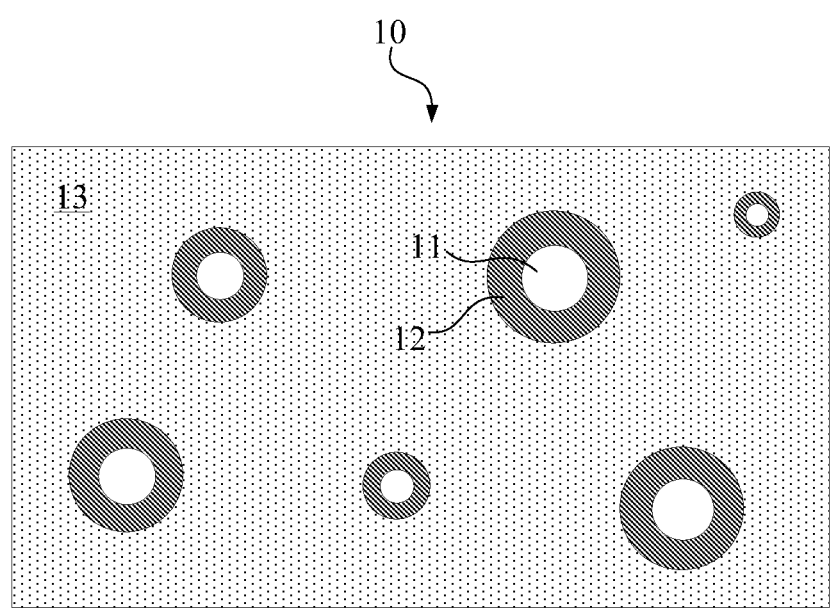
FIG. 1 is a schematic structural diagram showing an absorbable biomedical composite material according to a first embodiment of the present disclosure.

10—composite material; 11—substrate granule; 12—intermediate layer; 13—polymer matrix; 2—polylactic acid composite material; 20—core-shell structure; 21—substrate granule; 22—intermediate layer; 23—polymer layer; 30—polylactic acid matrix.

DETAILED DESCRIPTION OF THE EMBODIMENTS

Hereinafter, preferable embodiments of the present disclosure will be described in detail with reference to the accompanying drawings. In the following description, the same components are denoted by the same reference numerals, and the description thereof will be omitted. In addition, the drawings are exemplary where the component size and/or shape may be different from the actual ones.

In addition, for the sake of description, the subtitles are used in the following description. However, these subtitles merely serve as a hint for reading, and are not intended to limit the contents described under the subtitles to the subject of the subtitles.

First Embodiment (Composite Material)

Figure 2:
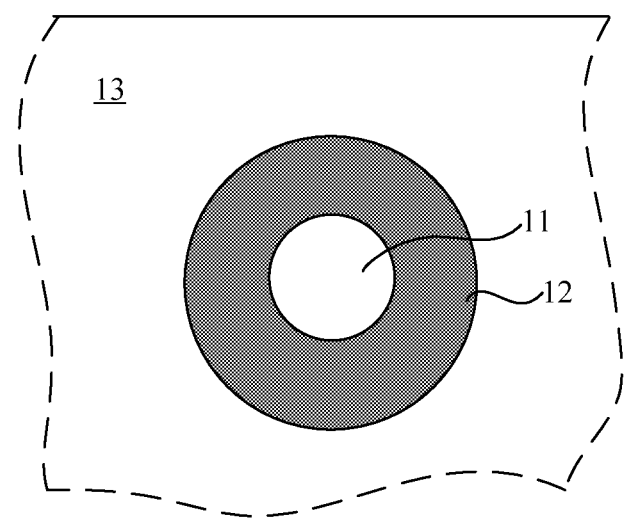
FIG. 2 is a structural schematic diagram showing part of the biomedical composite material according to the first embodiment of the present disclosure.

FIG. 1 is a schematic structural diagram showing an absorbable biomedical composite material according to a first embodiment of the present disclosure. FIG. 2 is a structural schematic diagram showing part of the biomedical composite material according to the first embodiment of the present disclosure.

As shown in FIGS. 1 and 2, the composite material 10 according to the first embodiment of the present disclosure may comprise substrate granules 11, intermediate layers 12 and a polymer matrix 13. To be specific, the outer surface of each substrate granule 11 is coated with an intermediate layer 12, and the polymer matrix is formed on the outer surface of the intermediate layer 12. In some examples, the substrate granules 11 with the respective intermediate layer 12 are uniformly distributed in the polymer matrix 13.

As described above, an intermediate layer 12 is formed between each substrate granule 11 and the polymer matrix 13. In this case, there is a buffer between the substrate granule 11 and the polymer matrix 13, so that the interfacial force between each substrate granule 11 and the polymer matrix 13 can be enhanced, and the substrate granules 11 may be better dispersed in the polymer matrix 13, thereby improving the mechanical strength and toughness of the composite material 1 simultaneously.

(Substrate Granule)

In the present embodiment, the substrate granules 11 may contain a calcium-phosphorus compound. Preferably, the substrate granules 11 may contain one or more selected from the group consisting of hydroxyapatite, calcium polyphosphate, and tricalcium phosphate. In this case, the bioactivity of the composite material 10 may be improved, providing better effect on human bone repair.

It is well known that calcium-phosphorus compounds are main inorganic constituents of human bones. When the composite material 10 according to the present embodiment is implanted into human body as the orthopedic material, the intermediate layer 12 and the polymer matrix 13 (described in detail later) will be absorbed by human body, and then calcium, phosphorus and some other elements contained in the substrate granules 11 will be absorbed by body tissues to form new bones, thereby contributing to bone growth and repair.

Further, the substrate granules 11 may be composed of compounds other than the above-described hydroxyapatite, calcium polyphosphate, tricalcium phosphate or the like. In the present embodiment, the composite material 10 can better repair human bones as long as the substrate granules 11 contain substances similar to the natural constituents of human bones.

In the present embodiment, preferably, the substrate granules 11 are rigid. In some examples, the substrate granules 11 may be rigid granules having a Young's modulus greater than $2 \times 10^{11}$ Pa. In this case, the mechanical strength of the composite material 10 may be effectively improved.

Further, in the present embodiment, the shape of the substrate granules 11 is not particularly restricted. For example, in some examples, the substrate granules 11 may be spherical. However, the present embodiment is not limited thereto, and in other examples, the substrate granules 11 may be ellipsoidal, or be irregular solids.

In the present embodiment, the content (wt %) of the substrate granules 11 is not particularly restricted. For the sake of mechanical strength and toughness of the composite material 10, the content of the substrate granules 11 is preferably from 1 wt % to 10 wt %. For example, the content of the substrate granules 11 may be 1 wt %, 3 wt %, 5 wt %, 8 wt % or 10 wt %. Specifically, in the composite material 10, the substrate granules 11 contribute to the mechanical strength of the composite material 10. Generally speaking, the more the content of the substrate granules 11 is, the higher the mechanical strength of the composite material 10 will be. When the content of the substrate granules 11 is relatively low, the mechanical strength of the composite material 10 is insufficient, while when too many substrate granules 11 are included in the composite material, the content of the polymer matrix 13 in the composite material 10 will be accordingly reduced, thereby decreasing the mechanical strength of the composite material 10. Therefore, when the composite material contains 1 wt % to 10 wt % of substrate granules 11, the mechanical strength of the composite material 10 will be improved, or at least the mechanical strength will not be badly affected or with minimum bad effect.

Further, in the present embodiment, the average granule size of the substrate granules 11 is not particularly restricted. For the mechanical strength and toughness of the composite material 10, the average granule size of the substrate granules 11 is preferably from 5 nm to 200 μm. For example, the average granule size of the substrate granules 11 may be 5 nm, 10 nm, 30 nm, 50 nm, 1 μm, 2 μm, 5 μm, 10 μm, 20 μm, 30 μm, 50 μm, 80 μm, 100 μm, 130 μm, 150 μm, 180 μm or 200 μm. Generally, the smaller the granule size is, the more rigid the substrate granules 11 will be. Therefore, when substrate granules 11 having relatively small granule size are selected, the substrate granules 11 will increase the mechanical strength of the composite material 10. As the granule size increases, the surface energy of the substrate granules 11 gradually decreases, and agglomeration can be suppressed to some extent. When the granule size is too large, the substrate granules may not be uniformly distributed in the polymer matrix, thereby badly affecting the mechanical strength of the composite material 1. Therefore, by limiting the granule size of the substrate granules 11 to the above range, the mechanical strength of the composite material 10 may be enhanced, and the dispersion of the substrate granules 11 is kept uniform.

(Intermediate Layer)

In the present embodiment, an intermediate layer 12 may be coated on the surface of each substrate granule 11. That is, an intermediate layer 12 covers the surface of each substrate granule 11. Additionally, the intermediate layer 12 may have a first glass transition temperature T1. In some examples, the first glass transition temperature T1 may be not higher than normal human body temperature. In general, when the environmental temperature is higher than the glass transition temperature of a polymer, the polymer will be in an elastic state or a rubbery state; while when the environmental temperature is lower than or equal to the glass transition temperature of the polymer, the polymer will be in a glassy state.

When the composite material 10 according to the present embodiment is applied to human body, since the first glass transition temperature T1 of the intermediate layer 12 is not higher than normal body temperature (for example, 37° C.), the intermediate layer 12 remains in the rubbery state. In this case, the rubbery intermediate layer 12 can release (for example, release in situ) the stress concentration caused by the substrate granules 11 and reduce the resulting microcracks, whereby the toughness of the composite material 10 may be improved. In addition, the substrate granules 11 may also fix (for example, fix in situ) the severe deformation of the rubbery intermediate layer 12 under a certain stress, whereby preventing the mechanical strength of the composite material 10 from decreasing.

In the present embodiment, the intermediate layer 12 may be composed of a polymer, and the intermediate layer 12 may be covalently bonded to each substrate granule 11. In this case, a strong interfacial force is formed between the substrate granules 11 and the intermediate layer 12, thereby improving the bonding force therebetween and facilitating the force transfer. In addition, the intermediate layer 12 may be bonded to the substrate granules 11 via a strong interfacial force such as ionic bonds.

In the clinical bone repair, the strong force between the rubbery intermediate layer 12 and the substrate granules 11 may enhance the force transfer between the intermediate layer 12 and the substrate granules 11 and to induce inductive coupling. On one hand, the rubbery intermediate layer 12 can release (for example, release in situ) the stress concentration caused by the substrate granules 11 and reduce the resulting microcracks, whereby the toughness of the composite material 10 can be improved; and on the other hand, the substrate granules 11 may also fix (for example, fix in situ) the severe deformation of the rubbery intermediate layer 12 under a certain stress, whereby the decrease in the mechanical strength of the composite material 10 caused by the addition of the rubbery intermediate layer 12 can be effectively suppressed. Therefore, the strength and toughness of the composite material 10 can be simultaneously improved, which is of important significance in the application of the composite material 10 of the present embodiment in orthopedic use.

In the present embodiment, the mass percent (wt %) of the intermediate layer 12 is not particularly restricted. For the sake of the mechanical strength and toughness of the composite material 10, the mass percent of the intermediate layer 12 is preferably from 1 wt % to 10 wt %. For example, the mass percent of the intermediate layer 12 may be 1 wt %, 3 wt %, 5 wt %, 8 wt % or 10 wt %. Specifically, in the composite material 10, the intermediate layer 12 functions to improve the toughness of the composite material 10. Generally speaking, the more the content of the intermediate layer 12 is, the higher the toughness of the composite material 10 will be. When the content of the intermediate layer 12 is relatively low, the toughness of the composite material 10 is insufficient, and when the content of the intermediate layer 12 is excessive, the composite material 10's mechanical strength and the like will be deteriorated. Therefore, when the mass percent of the intermediate layer 12 is set at 1 wt % to 10 wt %, the toughness of the composite material 10 can be improved, and there is no or almost no bad effect on the mechanical strength and other properties of the composite material 10.

In the present embodiment, the intermediate layer 12 may contain a homopolymer of p-dioxanone or caprolactone. The intermediate layer 12 may also contain a random copolymer or a block copolymer of two or more selected from the group consisting of lactide, caprolactone, p-dioxanone, and glycolide. In this case, the intermediate layer 12 may be made as an absorbable polymer material, which facilitates the application of the composite material 10 in the field of orthopedics, especially in the field of absorbable orthopedic materials.

As described above, in the present embodiment, the intermediate layer 12 has a first glass transition temperature T1 which may not be higher than normal human body temperature. In addition, the first glass transition temperature T1 is not particularly restricted. Preferably, the first glass transition temperature T1 ranges from $-40°$ C. to $36°$ C. ($-40°$ C.$\leq$T1$\leq$36° C.). For example, the first glass transition temperature T1 may be $-40°$ C., $-37°$ C., $-30°$ C., $-20°$ C., $-10°$ C., $-5°$ C., $0°$ C., $10°$ C., $20°$ C. or $36°$ C. More preferably, the first glass transition temperature T1 ranges from $-37°$ C. to $36°$ C. ($-37°$ C.$\leq$T1$\leq$36° C.).

In addition, in the present embodiment, the specific glass transition temperature T1 of the intermediate layer 12 may be adjusted according to actual needs. For a homopolymer, its glass transition temperature T1 may differ when the monomer species or its content is changed. For a copolymer, the glass transition temperature T1 may be changed by adjusting the content of each or several of the monomers.

Further, in the present embodiment, the molding method for the intermediate layer 12 is not particularly restricted. In some examples, the intermediate layer may be formed by in situ polymerization on the outer surfaces of the substrate granules 11. In addition, in some other examples, the intermediate layer may also be formed by modifying the surfaces of the substrate granules 11.

(Polymer Matrix)

In the present embodiment, the polymer matrix 13 is formed on the outer surface of the intermediate layer 12. Additionally, the polymer matrix 13 may have a second glass transition temperature T2. In some examples, the second glass transition temperature T2 may be higher than the first glass transition temperature T1 of the intermediate layer 12, i.e., T2>T1. In this way, the polymer matrix 13 has better mechanical strength than the intermediate layer 12 at a certain temperature, thereby enhancing the mechanical properties of the composite material 10.

In addition, in the present embodiment, the second glass transition temperature T2 of the polymer matrix 13 may be higher than normal body temperature. Thus, when the composite material 10 according to the present embodiment is applied to human body, the polymer matrix 13 remains in the glassy state, so that the composite material 10 has sufficiently high mechanical strength.

In the present embodiment, the polymer matrix 13 may be formed on the intermediate layer 12 in an in situ polymerization manner. In this case, a strong interfacial force such as covalent bonds can be formed between the intermediate layer 12 and the polymer matrix 13, thereby effectively improving the bonding force therebetween and facilitating the force transfer.

In the present embodiment, the intermediate layer 12 may be covalently bonded to the polymer matrix 13. In this case, a strong interfacial force is formed between the intermediate layer 12 and the polymer matrix 13, thereby effectively increasing the bonding force therebetween and facilitating the force transfer. In addition, the intermediate layer 12 may also be bonded to the polymer matrix 13 by a strong interfacial force such as ionic bonds.

Further, in the present embodiment, the polymer matrix 13 may contain a homopolymer of lactide, caprolactone, p-dioxanone, or glycolide. The polymer matrix 13 may also contain a random copolymer or a block copolymer of two or more selected from the group consisting of lactide, caprolactone, p-dioxanone, and glycolide. In this case, the polymer matrix 13 may be made as an absorbable polymer material that facilitates the application of the composite material 10 in the field of orthopedics, particularly in the field of absorbable orthopedic materials.

Figure 3:
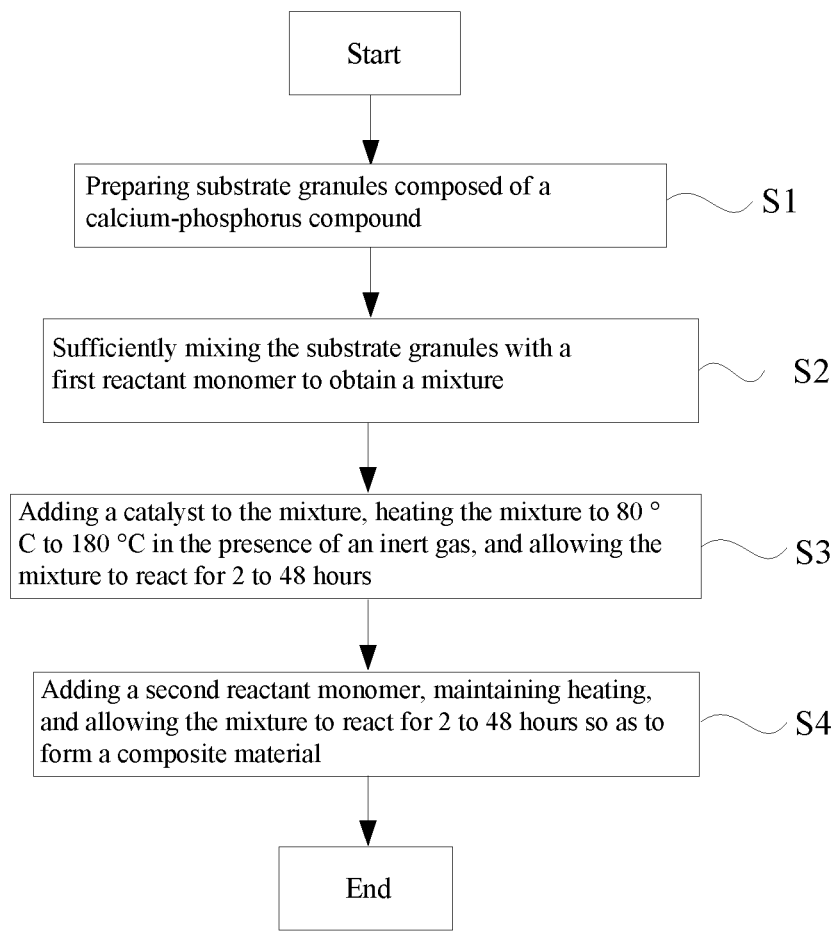
FIG. 3 is a schematic block diagram showing the steps of preparing the absorbable biomedical composite material.

FIG. 3 is a schematic diagram showing the steps of preparing the absorbable biomedical composite material.

Hereinafter, a method for preparing the absorbable biomedical composite material according to the present embodiment will be described in detail with reference to FIG. 3.

As shown in FIG. 3, the method for preparing the absorbable biomedical composite material according to the present embodiment may comprise the steps of: preparing substrate granules 11 composed of a calcium-phosphorus compound (step S1); sufficiently mixing the substrate granules 11 with a first reactant monomer to obtain a mixture (step S2); adding a catalyst to the mixture, heating the same to 80° C. to 180° C. in the presence of an inert gas, and allowing the mixture to react for 2 to 48 hours, such that an intermediate layer 12 composed of the first reactant monomer is coated on the substrate granules 11 (step S3); and adding a second reactant monomer, maintaining heating, and allowing the resultant mixture to react for another 2 to 48 hours to form a polymer matrix 13 on the intermediate layer 12 to finally obtain the composite material 10 (step S4).

In the present embodiment, in step S1, the substrate granules 11 composed of a calcium-phosphorus compound are first prepared. In some examples, the substrate granules 11 may be made of one or more selected from the group consisting of hydroxyapatite, calcium polyphosphate, and tricalcium phosphate. It is well known that calcium-phosphorus compounds are main inorganic constituents of human bones. After the composite material 10 according to the present embodiment is implanted into the body as an orthopedic repair material, the intermediate layer 12 and the polymer matrix 13 (described later) will be absorbed by human body, and therefore, calcium, phosphorus and other elements contained in the substrate granules 11 will be absorbed by body tissues to form new bones, thereby contributing to bone growth and repair.

Further, the substrate granules 11 may be composed of compounds other than the above-described hydroxyapatite, calcium polyphosphate, tricalcium phosphate or the like. In the present embodiment, the composite material 10 can better repair human bones as long as the substrate granules 11 contain substances similar to the natural constituents of the human bones.

In the present embodiment, in step S2, the substrate granules 11 prepared in step S1 may be sufficiently mixed with the first reactant monomer to obtain the mixture. In some examples, in step S2, the substrate granules 11 and the first reactant monomer may be dissolved in an organic solvent and thoroughly mixed to form the mixture. In other examples, the organic solvent is preferably 100% toluene.

The first reactant monomer may be one selected from the group consisting of lactide, caprolactone, p-dioxanone, and glycolide. The first reactant monomer may also be two or more selected from the group consisting of lactide, caprolactone, p-dioxanone, and glycolide. In this case, the resulting intermediate layer 12 is a homopolymer of p-dioxanone or caprolactone, or is a random copolymer or a block copolymer of two or more selected from the group consisting of lactide, caprolactone, p-dioxanone, and glycolide. Thus, the intermediate layer 12 may be made as an absorbable polymeric material that facilitates the application of the composite material 10 in the field of orthopedics, particularly in the field of absorbable orthopedic materials.

Further, in the present embodiment, in step S2, the first reactant monomer may be added as a whole or in several times. In some examples, after some monomers are added, the reaction proceeds for a period of time, and then additional monomers are added. In this way, a block polymer can be formed.

In the present embodiment, in step S3, a catalyst is added to the mixture obtained in step S2, which is heated to 80° C. to 180° C. in the presence of an inert gas, and the reaction is performed for 2 to 48 hours, such that the intermediate layer 12 composed of the first reactant monomer is coated on the substrate granules 11. In some examples, there is a strong force, such as covalent bonds, between the substrate granules 11 and the intermediate layer 12, and therefore the bonding force therebetween can be improved to facilitate force transmission and to induce inductive coupling.

Further, in the present embodiment, in step S3, the catalyst is preferably stannous octoate. In situ polymerization of monomers can be induced to generate a strong interfacial force such as covalent bonds.

Further, in the present embodiment, in step S3, the inert gas may be nitrogen gas or argon gas. With the inert gas, the reaction can be readily performed without generation of impurities.

In the present embodiment, in step S4, in the reaction system of step S3, the second reactant monomer is added, and the reaction is continued with heating for 2 to 48 hours, thereby forming a polymer matrix 13 on the intermediate layer 12 and finally obtaining the composite material 10.

The second reactant monomer may be one selected from the group consisting of lactide, caprolactone, p-dioxanone, and glycolide. Further, the second reactant monomer may be two or more selected from the group consisting of lactide, caprolactone, p-dioxanone, and glycolide. In this case, the resulting polymer matrix 13 is a homopolymer of lactide, caprolactone, p-dioxanone, or glycolide, or is a random copolymer or a block copolymer of two or more selected from the group consisting of lactide, caprolactone, p-dioxanone, and glycolide. Thus, the polymer matrix 13 can be made as an absorbable polymer material that facilitates the application of the composite material 10 in the field of orthopedics, particularly in the field of absorbable orthopedic materials.

In some examples, the second reactant monomer may be different from the first reactant monomer. They may differ in types, contents, or both.

Further, in the present embodiment, in step S4, the second reactant monomer may be added as a whole or in several times. In some examples, after some monomers are added, the reaction proceeds for a period of time, and then additional monomers are added. In this way, a block polymer can be formed.

Further, in the present embodiment, the products obtained in step S3 and step S4 are separately dissolved in a first organic solvent. Preferably, the first organic solvent is chloroform. Then, after centrifuging, the products are precipitated and washed in a second organic solvent. Preferably, the second organic solvent is methanol. A polymer for the intermediate layer 12 (the intermediate layer 12), a composition of the substrate granules 11 and the intermediate layer 12 (substrate granules 11-intermediate layer 12), and a composite material 10 containing the substrate granules 11, the intermediate layer 12 and the polymer matrix 13 (substrate granules 11-intermediate layer 12-polymer matrix 13) may be finally obtained.

In addition, in the present embodiment, the glass transition temperatures of certain materials may be tested by differential scanning calorimetry (DSC), and the weight-average molecular weights (Mw) of certain materials may be determined by gel permeation chromatography (GPC), and the content of certain components in the materials may be measured by thermogravimetric analysis (TGA).

In addition, in the present embodiment, the composite material 10 obtained in step S4 is subject to injection molding followed by mechanical property tests.

In the present embodiment, the absorbable biomedical composite material 10 prepared by step S1 to step S4 comprises the substrate granules 11 and the polymer matrix 13, and the intermediate layer 12 interposed between each substrate granule 11 and the polymer matrix 13. As described above, the glass transition temperature of the intermediate layer 12 is not higher than normal human body temperature. Therefore, when the composite material 10 according to the present embodiment is applied to clinic orthopedics, the intermediate layer 12 remains in a rubbery state inside the human body, such that the rubbery intermediate layer 12 may reduce the stress concentration and microcracks caused by the substrate granules 11, improving the toughness of the composite material 10. Meanwhile, the substrate granules 11 may also fix the severe deformation of the rubbery intermediate layer 12 under a certain stress, whereby preventing the mechanical strength of the composite material 10 from decreasing.

In order to further describe the present disclosure, the absorbable biomedical composite material and the preparation method therefor of the present disclosure will be described in detail below with reference to the examples, and the beneficial effects achieved by the present disclosure will be fully described in conjunction with the comparative examples.

Example 1

Hydroxyapatite of 0.1 g having a granule size of 5 nm, 0.06 g of L-lactide and 0.06 g of caprolactone were uniformly mixed and added with 40 µl of stannous octoate. The mixture was heated with stirring to 180° C. in the presence of nitrogen gas. After all components were melted, the mixture was stirred for 2 hours to form a hydroxyapatite-rubbery layer. Then, 10 g of L-lactide was added to the reaction system, and the reaction was continued at 180° C. for 2 hours.

After completion of the reaction, the obtained mixture was dissolved in chloroform, precipitated in methanol, and washed for three times with methanol, so that a hydroxyapatite-rubbery layer-polylactide composite material was obtained.

TABLE 1

| Sample | | Glass transition temperature (Tg, ° C.) | Weight-average molecular weight (Mw, g/mol) | Content of rubbery layer (wt %) |
|---|---|---|---|---|
| Example 1 | Rubbery layer | −7 | 3,000 | — |
|  | Rubbery layer-polylactide | 52 | 305,000 | 0.96 |
| Example 2 | Rubbery layer | 25 | 5,000 | — |
|  | Rubbery layer-polyglycolide | 40 | 40,300 | 9.93 |
| Example 3 | Rubbery layer | −37 | 4,500 | — |
|  | Rubbery layer-poly(lactide-co-glycolic acid) | 45 | 86,000 | 4.72 |
| Comparative Example 1 | Polylactide | 55 | 320,000 | — |
| Comparative Example 2 | Polylactide | 56 | 331,000 | — |

The obtained hydroxyapatite-rubbery layer composite material and hydroxyapatite-rubbery layer-polylactic acid composite material were separately dissolved in chloroform, and then centrifuged at 15000 rpm. The supernatant was poured into methanol for precipitation, and the precipitant was washed with methanol to obtain a free rubbery polymer and a rubbery-polylactic acid polymer, which were subject to further characterization. Differential scanning calorimetry (DSC) and gel permeation chromatography (GPC) data can be found in Table 1.

The hydroxyapatite-rubbery layer-polylactic acid composite material was subject to injection molding, and the mechanical property test results were shown in Table 2. The mass content of hydroxyapatite in the hydroxyapatite-rubbery layer-polylactic acid composite material was determined to be 1% by TGA. The mass content of the rubbery layer in the hydroxyapatite-rubbery layer-polylactic acid composite material was calculated using the weight-average molecular weights of the rubbery layer and the rubbery layer-polylactic acid in Table 1 in combination with the content of hydroxyapatite, and the results were shown in Table 1.

TABLE 2

| Sample | | Young's modulus (GPa) | Tensile strength (MPa) | Elongation at break (%) |
|---|---|---|---|---|
| Example 1 | Hydroxyapatite-rubbery layer-polylactide | 4.1 | 45.2 | 15.1 |
| Example 2 | Hydroxyapatite-rubbery layer-polyglycolide | 3.0 | 35.3 | 30.2 |
| Example 3 | Hydroxyapatite-rubbery layer-poly(lactide-co-glycolic acid) | 3.5 | 38.5 | 21.3 |
| Comparative Example 1 | Hydroxyapatite-polylactide | 5.5 | 60.2 | 2.1 |
| Comparative Example 2 | Hydroxyapatite-polylactide | 4.2 | 48.1 | 2.2 |
| Comparative example 3 | Polylactide | 3.5 | 40.1 | 6.1 |

Example 2

Hydroxyapatite of 1 g having a granule size of 200 µm, 0.4 g of L-lactide, 0.4 g of p-dioxanone and 0.4 g of glycolide were uniformly mixed in 100 ml of 100% toluene, and then added with 160 µl of stannous octoate. The mixture was heated under stirring to 80° C. in the presence of argon gas. The reactants were mixed and dissolved, and then stirred for 48 hours, to form hydroxyapatite-rubbery layer. Then, 8.5 g of glycolide was added to the reaction system, and the reaction was continued at 80° C. for 48 hours.

After completion of the reaction, the reaction mixture was precipitated in methanol, and washed for three times with methanol to obtain a hydroxyapatite-rubbery layer-polyglycolide composite material.

The obtained hydroxyapatite-rubbery layer composite material and the hydroxyapatite-rubbery layer-polyglycolide composite material were separately dissolved in chloroform, and then centrifuged at 15,000 rpm. The supernatant was poured into methanol for precipitation, and the precipitant was washed with methanol to obtain a rubbery polymer and a rubbery-polyglycolide polymer, which were subject to further characterization. Differential scanning calorimetry (DSC) and gel permeation chromatography (GPC) data can be found in Table 1.

The hydroxyapatite-rubbery layer-polyglycolide composite material was subject to injection molding, and the mechanical property test results were shown in Table 2. The mass content of hydroxyapatite in the hydroxyapatite-rubbery layer-polyglycolide composite material was determined to be 10% by TGA. The mass content of the rubbery layer in the hydroxyapatite-rubbery layer-polyglycolide composite material was calculated using the weight-average molecular weights of the rubbery layer and the rubbery layer-polylactic acid in Table 1 in combination with the content of hydroxyapatite, and the results were shown in Table 1.

Example 3

Hydroxyapatite of 0.5 g having a granule size of 200 nm and 0.3 g of caprolactone were uniformly mixed in 100 ml of 100% toluene, which was added with 100 μl of stannous octoate and heated under stirring to 120° C. in the presence of argon gas. The reactants were mixed and dissolved uniformly, and then allowed to react under stirring for 12 hours. The mixture was added with 0.3 g of p-dioxanone, and the reaction continued at 120° C. for 12 hours to form hydroxyapatite-rubbery layer. Then, 4.6 g of glycolide was added to the reaction system, and the reaction continued at 130° C. for 24 hours. Thereafter, with the addition of 4.6 g of L-lactide, the reaction continued at 130° C. for 24 hours.

After completion of the reaction, the reaction mixture was precipitated in methanol, and washed for three times with methanol to obtain a hydroxyapatite-rubbery layer-poly(lactide-co-glycolic acid) composite material.

The obtained hydroxyapatite-rubbery layer composite material and hydroxyapatite-rubbery layer-poly(lactide-co-glycolic acid) composite material were separately dissolved in chloroform, and then centrifuged at 15,000 rpm. The supernatant was precipitated in and washed with methanol to obtain a free rubbery polymer and a rubbery-poly(lactic-glycolic acid) polymer for further characterization. Differential scanning calorimetry (DSC) and gel permeation chromatography (GPC) data were shown in Table 1.

The hydroxyapatite-rubbery layer-poly(lactide-co-glycolic acid) composite material was subject to injection molding, and the mechanical property test results were shown in Table 2. The mass content of hydroxyapatite in the hydroxyapatite-rubbery layer-poly(lactide-co-glycolic acid) composite material was determined to be 5% by TGA. The mass content of the rubbery layer in the hydroxyapatite-rubbery layer-poly(lactide-co-glycolic acid) composite material was calculated using the weight-average molecular weights of the rubbery layer and the rubbery layer-polylactic acid in Table 1, in combination with the content of hydroxyapatite. The results were shown in Table 1.

Comparative Example 1

Hydroxyapatite of 0.1 g having a granule size of 5 nm and 10 g of L-lactide were uniformly mixed, added with 40 μl of stannous octoate was added, and then heated under stirring to 180° C. in the presence of nitrogen gas. The reaction mixture was melted and reacted under stirring for 2 hours, to form a hydroxyapatite-polylactic acid composite material.

After completion of the reaction, the reaction mixture was dissolved in chloroform and then precipitated in methanol, and washed for three times with methanol to obtain a hydroxyapatite-polylactic acid composite material.

The obtained hydroxyapatite-polylactic acid composite material was dissolved in chloroform, and then centrifuged at 15,000 rpm. The supernatant was precipitated in and washed with methanol to obtain free polylactic acid for characterization. Differential scanning calorimetry (DSC) and gel permeation chromatography (GPC) data were shown in Table 1.

The hydroxyapatite-polylactic acid composite material was subject to injection molding, and the mechanical property test results were shown in Table 2. The mass content of hydroxyapatite in the hydroxyapatite-polylactic acid composite material was determined to be 1% by TGA.

Comparative Example 2

Hydroxyapatite of 0.1 g having a granule size of 5 nm and 9.9 g of L-polylactic acid were dispersed and dissolved in chloroform, mixed with stirring, and then precipitated in methanol to obtain a hydroxyapatite-polylactic acid composite material.

The molecular weight and the glass transition temperature of the L-polylactic acid used in this comparative example were close to those in Comparative Example 1, and the differential scanning calorimetry (DSC) and gel permeation chromatography (GPC) data were shown in Table 1. The hydroxyapatite-polylactic acid composite material was subject to injection molding, and the mechanical property test results were shown in Table 2. The mass content of hydroxyapatite in the hydroxyapatite-polylactic acid composite material was determined to be 1.2% by TGA.

Comparative Example 3

The L-polylactic acid used in Comparative Example 2 was subject to injection molding, and the mechanical property test results were shown in Table 2.

As can be seen from Example 1 and Comparative Example 3 that the material design of the present disclosure can effectively increase both strength (Young's modulus and tensile strength) and toughness (elongation at break) of a polyester material.

As can be seen from Example 1 and Comparative Example 1, the buffering provided by the rubbery layer between hydroxyapatite and polylactic acid was helpful for improving the toughness of the polylactic acid material.

In Comparative Example 2, there was no strong interfacial force between the hydroxyapatite and the polylactic acid matrix. Thus, it can be seen from Example 1, Comparative Example 1 and Comparative Example 2 that a strong force at the interface of the absorbable composite material of the present disclosure played an important role in improving the mechanical properties of the composite material.

Second Embodiment (Polylactic Acid Composite Material)

Figure 4:
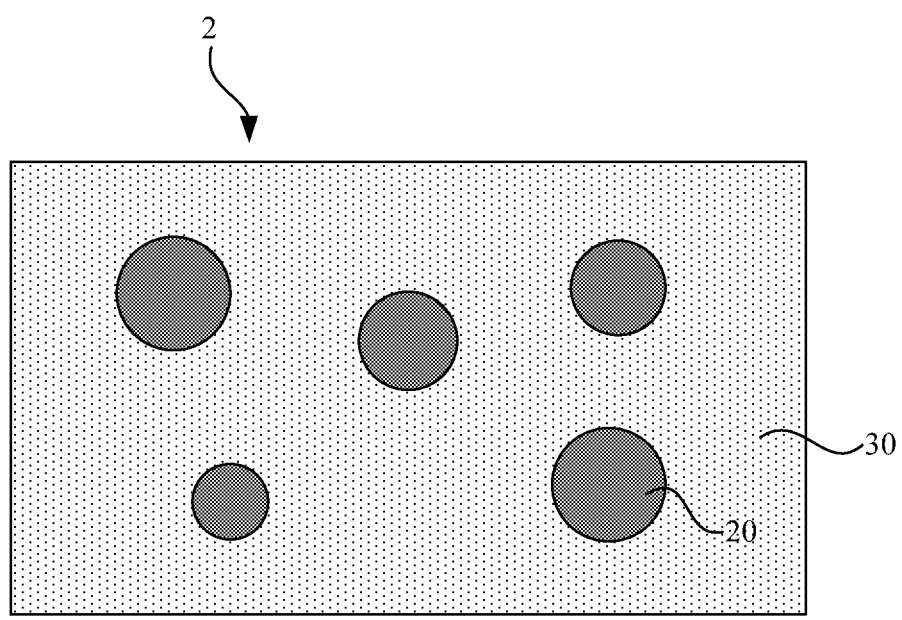
FIG. 4 is a schematic structural diagram showing an absorbable biomedical polylactic acid composite material according to a second embodiment of the present disclosure.

FIG. 4 is a schematic structural diagram showing an absorbable biomedical polylactic acid composite material according to a second embodiment of the present disclosure.

As shown in FIG. 4, the polylactic acid composite material 2 according to the present embodiment may comprise core-shell structures 20 and a polylactic acid matrix 30. In some examples, the core-shell structures 20 may be distributed in the polylactic acid matrix 30. Further, the polylactic acid matrix 30 may form a stereocomplex with each of the core-shell structures 20. In other words, the polylactic acid matrix 30 and the core-shell structures 20 may be bonded by a stereocomplex force, thereby providing good interfacial force and stability to the polylactic acid composite material 2.

The absorbable biomedical polylactic acid composite material 2 according to the present embodiment is particularly suitable for use in orthopedics. For example, the polylactic acid composite material 2 according to the present embodiment can be used as an orthopedic implant to repair human bones. The polylactic acid composite material 2 according to the present embodiment has excellent bioactivity and may promote bone growth and repair. On the other hand, the material can be absorbed and metabolized by human body, and is thus favored in orthopedics.

(Core-Shell Structure)

Figure 5:
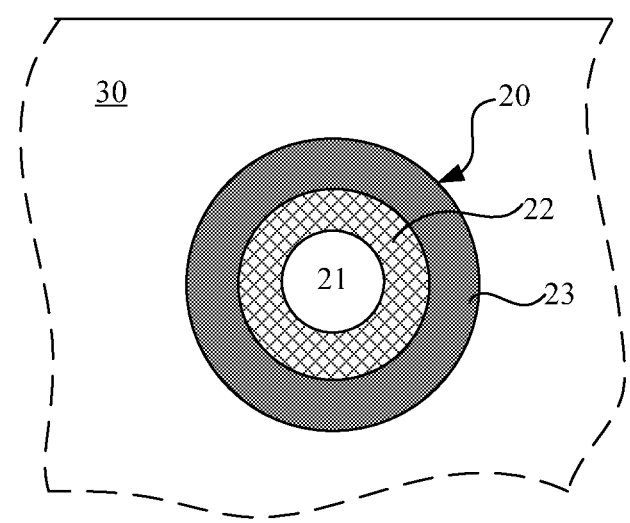
FIG. 5 is a schematic sectional diagram showing a core-shell structure in the polylactic acid composite material according to the second embodiment of the present disclosure.

FIG. 5 is a schematic sectional diagram showing a core-shell structure in the polylactic acid composite material according to the second embodiment of the present disclosure.

As shown in FIG. 5, in the present embodiment, the core-shell structure 20 may comprise a substrate granule 21, an intermediate layer 22, and a polymer layer 23. Specifically, in the core-shell structure 20, the outer surface of the substrate granule 21 is covered with an intermediate layer 22, and a polymer layer 23 is formed on the outer surface of the intermediate layer 22. In some examples, multiple core-shell structures 20 may be uniformly dispersed in the polylactic acid matrix 30. In this case, with the surface-modified substrate granules 21, when the core-shell structures 20 are added to the polylactic acid matrix 30, the interfacial force between the substrate granules 21 and the polylactic acid matrix 30 will be enhanced, the substrate granules 21 may be more evenly distributed in the polylactic acid matrix 30. The mechanical strength and toughness of the polylactic acid composite material 2 may be also improved.

In the present embodiment, the substrate granule 21, the intermediate layer 22, and the polymer layer 23 in each core-shell structure 20 may correspond to the substrate granules 11, the intermediate layer 12, and the polymer matrix 13 in the first embodiment, respectively, and may, for example, be made of the same material.

(Substrate Granule)

In the present embodiment, the substrate granules 21 may contain a calcium-phosphorus compound. Preferably, the substrate granules 21 may contain one or more selected from the group consisting of hydroxyapatite, calcium polyphosphate, and tricalcium phosphate. In this case, the bioactivity of the polylactic acid composite material 2 may be improved, providing better effect on human bone repair.

It is well known that calcium-phosphorus compounds are the main inorganic constituents of human bones. When the polylactic acid composite material 2 according to the present embodiment is implanted into human body as the orthopedic material, the intermediate layer 22 and the polymer layer 23 (described in detail later) will be absorbed by human body, and then calcium, phosphorus and some other elements contained in the substrate granules 21 will be absorbed by body tissues to form new bones, thereby contributing to bone growth and repair.

Further, the substrate granules 21 may be composed of compounds other than the above-described hydroxyapatite, calcium polyphosphate, tricalcium phosphate or the like. In the present embodiment, the polylactic acid composite material 2 can better repair human bones as long as the substrate granules 21 contain substances similar to the natural constituents of the human bones.

In the present embodiment, preferably, the substrate granules 21 are rigid. In some examples, the substrate granules 21 may be rigid granules having a Young's modulus greater than $2 \times 10^{11}$ Pa. In this case, the mechanical strength of the polylactic acid composite material 2 may be effectively improved.

Further, in the present embodiment, the shape of the substrate granules 21 is not particularly restricted. For example, in some examples, the substrate granules 21 may be spherical. However, the present embodiment is not limited thereto, and in other examples, the substrate granules 21 may be ellipsoidal, or be irregular solids.

In the present embodiment, the content (wt %) of the substrate granules 21 is not particularly restricted. For the sake of mechanical strength and toughness of the polylactic acid composite material 2, the content of the substrate granules 21 is preferably from 1 wt % to 30 wt %. For example, the content of the substrate granules 21 may be 1 wt %, 3 wt %, 5 wt %, 8 wt %, 15 wt %, 20 wt %, 25 wt % or 30 wt %. Specifically, in the polylactic acid composite material 2, the substrate granules 21 contribute to the mechanical strength of the polylactic acid composite material. Generally speaking, the more the content of the substrate granules 21 is, the higher the mechanical strength of the polylactic acid composite material 2 will be. When the content of the substrate granules 21 is relatively low, the mechanical strength of the polylactic acid composite material 2 may be insufficient, while when too many substrate granules 21 are included in the composite material, the toughness of the polylactic acid composite material 2 may decrease. Therefore, when the composite material contains 1 wt % to 30 wt % of substrate granules 21, the mechanical strength of the polylactic acid composite material 2 will be improved, or at least the toughness will not be badly affected or with minimum bad effect.

Further, in the present embodiment, the average granule size of the substrate granules 21 is not particularly restricted. For the mechanical strength and toughness of the polylactic acid composite material 2, the average granule size of the substrate granules 21 is preferably from 5 nm to 200 μm. For example, the average granule size of the substrate granules 21 may be 5 nm, 10 nm, 30 nm, 50 nm, 1 μm, 2 μm, 5 μm, 10 μm, 20 μm, 30 μm, 50 μm, 80 μm, 100 μm, 130 μm, 150 μm, 180 μm or 200 μm. Generally, the smaller the granule size is, the more rigid the substrate granules 21 will be. Therefore, when substrate granules 21 having relatively small granule size are selected, the substrate granules 21 will increase the mechanical strength of the polylactic acid composite material 2. As the granule size increases, the surface energy of the substrate granules 21 gradually decreases, and agglomeration can be suppressed to some extent. When the granule size is too large, the substrate granules may not uniformity distributed in the polylactic acid matrix, thereby affecting the mechanical strength of the polylactic acid composite material 2. Therefore, by limiting the granule size of the substrate granules 21 to the above range, the mechanical strength of the polylactic acid composite material 2 can be enhanced, and the dispersion of the substrate granules 21 is kept uniform.

(Intermediate Layer)

In the present embodiment, an intermediate layer 22 may be coated on the surface of each substrate granule 21. That is, the intermediate layer 22 covers the surface of each substrate granule 21. Additionally, the intermediate layer 22 may have a fourth glass transition temperature T4. In some examples, the fourth glass transition temperature T4 may be not higher than normal human body temperature. In general, when the external temperature is higher than the glass transition temperature of a polymer, the polymer will be in an elastic state or a rubbery state; while when the external temperature is lower than or equal to the glass transition temperature of the polymer, the polymer will be in a glassy state.

When the polylactic acid composite material 2 according to the present embodiment is applied to human body, since the fourth glass transition temperature T4 of the intermediate layer 22 is not higher than normal body temperature (for example, 37° C.), the intermediate layer 22 remains in the rubbery state. In this case, the rubbery intermediate layer 22 can release (for example, release in situ) the stress concentration caused by the substrate granules 21 and reduce the resulting microcracks, whereby the toughness of the polylactic acid composite material 2 can be improved. In addition, the substrate granules 21 may also fix (for example, fix in situ) the severe deformation of the rubbery intermediate layer 22 under a certain stress, whereby preventing the mechanical strength of the polylactic acid composite material 2 from decreasing.

In the present embodiment, the intermediate layer 22 may contain a homopolymer of p-dioxanone or caprolactone. Moreover, the intermediate layer 22 may also contain a random copolymer or a block copolymer of two or more selected from the group consisting of lactide, caprolactone, p-dioxanone, and glycolide. In this case, the intermediate layer 22 may be made as an absorbable polymer material, which facilitates the application of the polylactic acid composite material 2 in orthopedics, especially in the field of absorbable orthopedic materials.

As described above, in the present embodiment, the intermediate layer 22 has a fourth glass transition temperature T4 which may not be higher than normal human body temperature. In addition, the fourth glass transition temperature T4 is not particularly restricted. Preferably, the fourth glass transition temperature T4 ranges from −37° C. to 36° C. (−37° C.≤T4≤36° C.), more preferably, from −10° C. to 36° C. (−10° C.≤T4≤36° C.).

In addition, in the present embodiment, the specific glass transition temperature T4 of the intermediate layer 22 may be adjusted according to actual needs. For a homopolymer, its glass transition temperature T4 may differ when the monomer species or its content is changed. For a copolymer, the glass transition temperature T4 may be changed by adjusting the mass percent occupied by each or several of the monomers.

In the present embodiment, the intermediate layer 22 may be composed of a polymer. In this case, the substrate granule 21 and the intermediate layer 22 may be covalently bonded to form a strong interface force between the substrate granule 21 and the intermediate layer 22, thus effectively elevating the bonding force between these two, which facilitates the force transfer. In addition, the substrate granules 21 may also be bonded to the intermediate layer 22 by a strong interfacial force such as ionic bonds.

In the clinical human orthopedics, a strong force between the rubbery intermediate layer 22 and the substrate granules 21 may contribute to the force transfer between the intermediate layer 22 and the substrate granules 21 and to induce inductive coupling. To be specific, on one hand, the rubbery intermediate layer 22 can release (for example, release in situ) the stress concentration and alleviate the resulting microcracks caused by the substrate granules 21, whereby the toughness of the polylactic acid composite material 2 can be improved. On the other hand, the substrate granules 21 may suppress (for example, suppress in situ) the severe deformation of the rubbery intermediate layer 22 under a certain stress, whereby the decrease in the mechanical strength of the polylactic acid composite material 2 caused by the addition of the rubbery intermediate layer 22 can be suppressed. Therefore, the strength and toughness of the polylactic acid composite material 2 can be simultaneously improved, which is of important significance in the application of the polylactic acid composite material 2 according to the present embodiment as orthopedic medical devices.

Further, in the present embodiment, the molding method for the intermediate layer 22 is not particularly restricted. In some examples, the intermediate layer may be formed by in situ polymerization on the outer surfaces of the substrate granules 21. In addition, in some other examples, the intermediate layer may also be formed by modifying the surfaces of the substrate granules 21.

(Polymer Layer)

In the present embodiment, a polymer layer 23 is formed on the outer surface of the intermediate layer 22. A stereocomplex may be formed between the polymer layer 23 and the polylactic acid matrix 30 (described later). In general, the stereocomplex contains special hydrogen bonds, i.e., stereocomplex force, which are more stable than common hydrogen bonds, and thus has a higher melting point and better mechanical properties.

In the present embodiment, in the stereocomplex formed between the polymer layer 23 and the polylactic acid matrix 30, the stereocomplex force between the polymer layer 23 and the polylactic acid matrix 30 contributes to the force transfer between the polylactic acid matrix 30 and the rubbery intermediate layer 22 and is thus capable of improving the mechanical strength of the polylactic acid composite material 2. In addition, the stereocomplex force can also improve the dispersion of the core-shell structures 20 in the polylactic acid matrix 30, thereby enhancing both the mechanical strength and toughness of the polylactic acid composite material 2.

In addition, in the present embodiment, the molding method of the polymer layer 23 is not particularly restricted. Preferably, the polymer layer may be formed by in situ polymerization on the outer surface of the intermediate layer 22.

In the present embodiment, the polymer layer 23 may contain a homopolymer of a first type of lactide. Moreover, the polymer layer 23 may alternatively contain a random copolymer or a block copolymer of a first type of lactide with one or more monomers selected from the group consisting of a second type of lactide, caprolactone, p-dioxanone, and glycolide. Therefore, the polymer layer 23 may be formed as poly(L-lactic acid) or poly(D-lactic acid), or a copolymer having poly(L-lactic acid) or poly(D-lactic acid), so as to form a stereocomplex with the polylactic acid matrix 30 to provide a stereocomplex force therebetween.

Further, in the present embodiment, the molecular weight of the polymer layer 23 is not particularly restricted. For example, the polymer layer 23 may have a relatively small molecular weight to form a short-chain polymer layer 23, or the polymer layer 23 may have a relatively large molecular weight to form a long-chain polymer layer 23.

In addition, in the present embodiment, the glass transition temperature of the polymer layer 23 is not particularly restricted. Optionally, the glass transition temperature of the polymer layer 23 may be the same as that of the intermediate layer 22, or may be higher or lower than that of the intermediate layer 22.

(Polylactic Acid Matrix)

In the present embodiment, the polylactic acid matrix 30 may form a stereocomplex with the polymer layer 23 of the core-shell structure 20. As described above, the stereocomplex contains special hydrogen bonds, i.e., stereocomplex force, which are more stable than common hydrogen bonds, and thus has a higher melting point and better mechanical properties. In addition, the stereocomplex force of the stereocomplex contributes to the force transfer between the polylactic acid matrix 30 and the rubbery intermediate layer 22 and is thus capable of improving the dispersion of the core-shell structures 20 in the polylactic acid matrix 30, thereby improving the mechanical strength and toughness of the polylactic acid composite material 2 simultaneously.

In the present embodiment, the polylactic acid matrix 30 may contain a plurality of core-shell structures 20, and the plurality of core-shell structures 20 may be dispersed in the polylactic acid matrix 30. In addition, the size of the core-shell structure 20 is not particularly restricted. In some examples, the plurality of core-shell structures 20 may be uniform in size, and in other examples, the plurality of core-shell structures 20 may have different sizes.

In the present embodiment, the polylactic acid matrix 30 may have a third glass transition temperature T3. In addition, the third glass transition temperature T3 may be higher than the fourth glass transition temperature T4 of the intermediate layer 22 of the core-shell structure 20. That is, T3>T4. Thus, at the same temperature, the polylactic acid matrix 30 may have better mechanical strength than the core-shell structure 20, thereby enhancing the mechanical properties of the polylactic acid composite material 2.

Further, in the present embodiment, the third glass transition temperature T3 of the polylactic acid matrix 30 may be higher than normal body temperature. Therefore, when the polylactic acid composite material 2 according to the present embodiment is applied to human body, it may remain in a glassy state, such that the mechanical strength of the polylactic acid composite material 2 can be high enough.

In the present embodiment, the polylactic acid matrix 30 may contain a homopolymer of a second type of lactide. Moreover, the polylactic acid matrix 30 may also contain a random copolymer or a block copolymer of the second type of lactide with one or more monomers selected from the group consisting of a first type of lactide, caprolactone, p-dioxanone, and glycolide. In some examples, one of the first type of lactide and the second type of lactide is L-lactide, and the other is D-lactide.

In this case, the polylactic acid matrix 30 and the polymer layer 23 of the core-shell structure 20 can be formed with L-polylactic acid and D-polylactic acid, or alternatively D-polylactic acid and L-polylactic acid, respectively. When the polylactic acid matrix 30 is in contact with the polymer layer 23 of the core-shell structure 20, special hydrogen bonds (stereocomplex force) that are more stable than common hydrogen bonds will be generated, and thereby a stereocomplex is formed. Since the stereocomplex has a higher melting point and better mechanical properties than pure poly-L-lactide or poly-D-lactide, the mechanical properties of the polylactic acid composite material 2 may be further improved.

As described above, in the present embodiment, the polymer layer 23 of the core-shell structure 20 may form a stereocomplex with the polylactic acid matrix 30. In the stereocomplex, the stereocomplex crystallization ratio is not particularly restricted. In some examples, for the sake of the mechanical properties, the stereocomplex crystallization ratio is preferably from 1% to 40%. For example, the stereocomplex crystallization ratio may be 1%, 5%, 10%, 20%, 30% or 40%. In general, the higher the stereocomplex crystallization ratio is, the more stereocomplexes will be formed in the composite material and the stronger the corresponding stereocomplex force will be, that is, the stronger the mechanical properties of the composite material will be.

Figure 6:
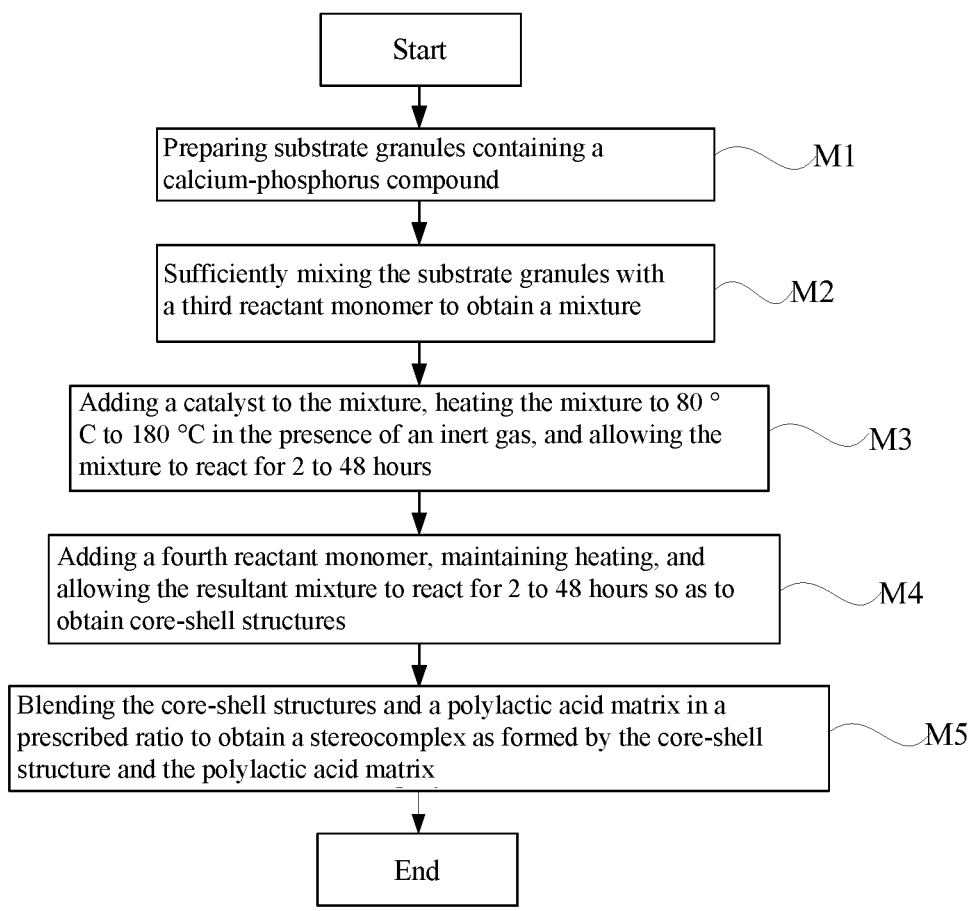
FIG. 6 is a schematic block diagram showing the steps of preparing the absorbable biomedical polylactic acid composite material according to the second embodiment of the present disclosure.

FIG. 6 is a schematic diagram showing a method of preparing an absorbable biomedical polylactic acid composite material.

Hereinafter, the method for preparing the absorbable biomedical polylactic acid composite material according to the present embodiment will be described in detail with reference to FIG. 6.

As shown in FIG. 6, the method for preparing the absorbable biomedical polylactic acid composite material according to the present embodiment comprises the steps of preparing substrate granules 21 containing a calcium-phosphorus compound (step M1); sufficiently mixing the substrate granules 21 with a third reactant monomer to obtain a mixture (step M2); adding a catalyst to the mixture, and heating the mixture to 80° C. to 180° C. in the presence of an inert gas, and allowing the mixture to react for 2 to 48 hours, such that an intermediate layer 22 composed of the third reactant monomer is coated on the substrate granules 21 (step M3); adding a fourth reactant monomer, maintaining heating, and allowing the mixture to react for 2 to 48 hours to form a polymer layer 23 on the intermediate layer, thereby obtaining core-shell structures 20 (step M4); and blending the core-shell structures 20 and a polylactic acid matrix 30 in a predetermined ratio to generate a stereocomplex formed by the core-shell structure 20 and the polylactic acid matrix 30, thereby obtaining a polylactic acid composite material 2 (step M5).

In the present embodiment, in step M1, the substrate granules 21 containing the calcium-phosphorus compound are first prepared. In some examples, the substrate granules 21 may be one or more selected from the group consisting of hydroxyapatite, calcium polyphosphate, and tricalcium phosphate. It is well known that among inorganic constituents of human bone tissues, calcium-phosphorus compounds are the dominant ones. After the polylactic acid composite material 2 according to the present embodiment is implanted into human body as an orthopedic repair material, the intermediate layer 22 and the polymer layer 23 (described later) will be absorbed by human body, and therefore, elements such as calcium and phosphorus contained in the substrate granules 21 will be absorbed by body tissues to form new bones, thereby promoting bone growth and repair.

Further, the substrate granules 21 are not limited to the above-described hydroxyapatite, calcium polyphosphate, tricalcium phosphate or the like. In the present embodiment, the substrate granules 21 may improve the repairing effect of the polylactic acid composite material 2 on the human bones as long as the substrate granules 21 contain substances similar to the constituents of the human bones.

In the present embodiment, in step M2, the substrate granules 21 obtained in step M1 may be sufficiently mixed with the third reactant monomer to obtain the mixture. In some examples, in step M2, the substrate granules 21 may be firstly dissolved in an organic solvent, and then added and sufficiently mixed with the first reactant monomer to form an organic mixture.

In the present embodiment, in step M3, the catalyst is added to the mixture obtained in step M2, which was heated to 80° C. to 180° C. in the presence of an inert gas and allowed to react for 2 to 48 hours to obtain the intermediate layer 22 coated on the surface of each matrix granule 21.

The third reactant monomer may be one of lactide, caprolactone, p-dioxanone, and glycolide. Further, the third reactant monomer may be two or more selected from the group consisting of lactide, caprolactone, p-dioxanone, and glycolide. In this case, the resulting intermediate layer 22 is a homopolymer of p-dioxanone or caprolactone, or is a random copolymer or a block copolymer of two or more selected from the group consisting of lactide, caprolactone, and p-dioxanone, and glycolide. Thus, the intermediate layer 22 can be formed as an absorbable polymeric material that facilitates the use of the polylactic acid composite material 2 in orthopedics, particularly as an absorbable orthopedic material.

In the present embodiment, the intermediate layer 22 may be composed of a polymer, and the substrate granules 21 may be covalently bonded to the intermediate layer 22. In clinical human orthopedics, a strong force between the rubbery intermediate layer 22 and the substrate granules 21 facilitates the force transfer and induce inductive coupling. To be specific, on one hand, the rubbery intermediate layer 22 can in situ release the stress concentration and reduce microcracks caused by the substrate granules 21, whereby to improve the toughness of the polylactic acid composite material 2. On the other hand, the substrate granules 21 may also in situ suppress the severe deformation of the rubbery intermediate layer 22 under a certain stress, whereby the decrease in the mechanical strength of the polylactic acid composite material 2 caused by the addition of the rubbery intermediate layer 22 can be effectively avoided. In summary, that the intermediate layer 22 and the substrate granules 21 are covalently bonded brings excellent force transfer and inductive coupling, such that the mechanical strength and toughness of the polylactic acid composite material 2 can be enhanced, which is of important significance in the use of orthopedic medical devices.

Further, in step M3, the catalyst is preferably stannous octoate, with which in-situ polymerization of monomers can be initiated to form a strong interfacial force such as covalent bonds.

Further, in the present embodiment, the inert gas may be nitrogen gas or argon gas. With the inert gas, the reaction may go smoothly, and the formation of impurities can be effectively avoided.

In the present embodiment, in step M4, a fourth reactant monomer was added to the reaction system obtained in step M3, and with continued heating the reaction was performed for another 2 to 48 hours, thereby forming a polymer layer 23 on the intermediate layer 22 and finally obtaining the core-shell structure 20.

The third reactant monomer may be a first type of lactide, or a first type of lactide with one or more selected from the group of a second type of lactide, caprolactone, p-dioxanone, and glycolide. In this case, the resulting polymer layer 23 is a homopolymer of the first type of lactide, or a random copolymer or a block copolymer of the first type of lactide with one or more monomers selected from the group consisting of the second type of lactide, caprolactone, p-dioxanone, and glycolide.

Further, in the present embodiment, the products from step M3 and step M4 are separately dissolved in organic solvents. Preferably, the organic solvent is chloroform. Next, free molecular chains not attached to the substrate granules 21 are separated and removed via centrifugation, such that a composition of the matrix granules 21 and the intermediate layer 22 (substrate granule 21-intermediate layer 22), and core-shell structures 20 are obtained respectively. The removed free molecular chains, i.e., the intermediate layer 22 and the composition of the intermediate layer 22 and the polymer layer 23 (intermediate layer 22-polymer layer 23) were subject to DSC tests to detect the glass transition temperatures of these materials.

In the present embodiment, in step M5, the core-shell structures 20 prepared in step M4 are mixed with the polylactic acid matrix 30 in a predetermined ratio to obtain a stereocomplex formed by the core-shell structure 20 and the polylactic acid matrix 30, and therefore the polylactic acid composite material 2 is obtained.

The polylactic acid matrix 30 may contain a homopolymer of the second type of lactide. The polylactic acid matrix 30 may contain a random copolymer or a block copolymer of the second type of lactide with one or more monomers selected from the group consisting of the first type of lactide, caprolactone, p-dioxanone, and glycolide, wherein one of the first type of lactide and the second type of lactide is L-lactide, and the other is D-lactide. In this case, the polymer layer 23 and the polylactic acid matrix 30 are formed as L-lactide and D-polylactide, or alternatively D-polylactide and L-lactide, respectively. When they are in contact, special hydrogen bonds which are more stable than common hydrogen bonds are generated, and a stereocomplex is formed. Such a stereocomplex has a higher melting point and better mechanical properties than pure poly(L-lactic acid) or poly(D-lactic acid), and the mechanical properties of the polylactic acid composite material can be further improved.

Therefore, the core-shell structure 20 containing the polymer layer 23 forms a stereocomplex force with the polylactic acid matrix 30, which facilitates the force transfer between the polylactic acid matrix 30 and the intermediate layer 22 of the core-shell structure 20 and the dispersion of the substrate granules 21 of the core-shell structure 20 in the polylactic acid matrix 30. Such material structure design can bring excellent force transfer and induce inductive coupling, such that the mechanical strength and toughness of the polylactic acid composite material 2 can be improved, which is of great significance in the use of orthopedic medical devices.

Further, as described above, in step M5, the organic solvent (the first organic solvent) in which the core-shell structure 20 and the polylactic acid matrix 30 are blended may be chloroform. Further, in step S5, the organic solvent (the second organic solvent) in which the reaction system is precipitated to obtain the polylactic acid composite material 2 may be methanol. Further, in the present embodiment, the first organic solvent is different from the second organic solvent.

Further, in the present embodiment, the polylactic acid composite material 2 obtained in step M5 is subject to injection molding, and its mechanical properties are tested.

In the present embodiment, the absorbable biomedical polylactic acid composite material 2 prepared by step M1 to step M5 comprises the core-shell structures 20 and the polylactic acid matrix 30 that forms a stereocomplex force with the core-shell structure 20. The stereocomplex force not only helps the force transfer between the polylactic acid matrix 30 and the core-shell structure 20, but also promotes the dispersion of the core-shell structures 20 in the polylactic acid matrix 30.

Further, in the core-shell structure 20, an intermediate layer 22 is further provided between the substrate granule 21 and the polymer layer 23. As described above, the glass transition temperature of the intermediate layer 22 is not higher than normal body temperature. Therefore, when the polylactic acid composite material 2 according to the present embodiment is applied in clinical orthopedics, the intermediate layer 22 of the core-shell structure 20 can maintain in a rubbery state inside human body, and the rubbery intermediate layer 22 can release the stress concentration and reduce the resulting microcracks caused by the substrate granules 21, whereby the toughness of the polylactic acid composite material 2 can be improved. Meanwhile, the substrate granules 21 may also suppress the severe deformation of the rubbery intermediate layer 22 under a certain stress, whereby the decrease in the mechanical strength of the polylactic acid composite material 2 can also be suppressed.

To further describe the present disclosure, the absorbable biomedical polylactic acid composite material and its preparation method therefor of the present disclosure are described in detail below with reference to the examples, and the beneficial effects achieved by the present disclosure are fully described in conjunction with the comparative examples.

Example 4

Hydroxyapatite of 2 g having a granule size of 5 nm was dispersed in 100 ml of toluene, which was added with 9 g of caprolactone, 6 g of L-lactide and 160 μl of stannous octoate. The mixture was heated under stirring to 80° C. in the presence of an inert gas, and the reaction was performed for 2 hours. Then, 5 g of D-lactide was added to the mixture, and the reaction was continued for 2 hours.

The products obtained in the above two stages were dissolved separately in chloroform, and free molecular chains not attached to hydroxyapatite were removed by centrifugation to obtain a hydroxyapatite-rubbery layer polymer (hydroxyapatite-rubbery layer), and core-shell structures composed of hydroxyapatite, a rubbery layer and poly(D-lactic acid). The removed free molecular chains, i.e., the rubbery molecular chains and the rubbery layer-poly(D-lactic acid) polymer molecular chains were subject to DSC tests to detect the glass transition temperatures of these materials. The results were shown in Table 3.

TABLE 3

| Sample | | Glass transition temperature (Tg, ° C.) |
|---|---|---|
| Example 4 | Rubbery layer | −35 |
| | Rubbery layer-poly-D-lactide | −16 |

TABLE 3-continued

| Sample | | Glass transition temperature (Tg, ° C.) |
|---|---|---|
| Example 5 | Rubbery layer | −10 |
| | Rubbery layer-poly(D-lactide-co-caprolactone) random copolymer | 40 |
| Example 6 | Rubbery layer | −37 |
| | Rubbery layer-poly(D-lactide-co-glycolide) block copolymer | 17 |
| Comparative Example 4 | Rubbery layer | −35 |
| | Rubbery layer-poly-L-lactide | −17 |
| Comparative Example 5 | Poly-D-lactide | 55 |

Finally, the core-shell structures and the poly(L-lactic acid) (Mn=120,000, glass transition temperature of 55° C.) were blended in chloroform, and precipitated in methanol to obtain a polylactic acid composite material. The composite material was subject to injection molding followed by mechanical property tests. The results were shown in Table 4.

For the polylactic acid composite material, the mass percent of hydroxyapatite was 1% as measured in the TGA test, and the stereocomplex crystallization ratio of the polylactic acid composite material was 1% as measured in the DSC test.

TABLE 4

| Sample | Young's modulus (GPa) | Tensile strength (MPa) | Elongation at break (%) |
|---|---|---|---|
| Example 4 | 3.8 | 44.1 | 12.9 |
| Example 5 | 4.6 | 52.2 | 26.1 |
| Example 6 | 4.5 | 50.1 | 21.2 |
| Comparative Example 4 | 3.4 | 42.2 | 8.4 |
| Comparative Example 5 | 4.0 | 46.2 | 2.4 |
| Comparative example 6 | 3.2 | 38.2 | 4.2 |

Example 5

Calcium polyphosphate of 2 g having a granule size of 200 μm was dispersed in 8 g of p-dioxanone, to which 160 μl of stannous octoate was then added. The mixture was heated with stirring to 180° C. in the presence of an inert gas, and the reaction was performed for 48 hours. Then, 5 g of D-lactide and 1 g of caprolactone were added to the mixture, and the reaction was continued for 48 hours.

The products from the two stages were separately dissolved in chloroform, and free molecular chains not attached to calcium polyphosphate were removed by centrifugation. A calcium polyphosphate-rubbery polymer (calcium polyphosphate-rubbery layer), and core-shell structures composed of calcium polyphosphate, a rubbery layer and poly(D-lactide-co-caprolactone) random copolymer were obtained. The removed free molecular chains, i.e., the rubbery layer molecular chains and the rubbery layer-poly(D-lactide-co-caprolactone) random copolymer molecular chains were subject to DSC tests to detect the glass transition temperature. The results were shown in Table 3.

The polylactic acid matrix was obtained by the following method. In specific, 25 mg of ethylene glycol, 160 μl of stannous octoate, 45 g of L-lactide and 5 g of caprolactone were heated under stirring to 180° C., reacted for 48 hours, and then purified by a chloroform-methanol system, wherein the obtained polylactic acid matrix was a poly(L-lactide-cocaprolactone) random copolymer (Mn=110,000, glass transition temperature of 50° C.).

The core-shell structures and the polylactic acid matrix were blended in chloroform and precipitated in methanol to obtain a polylactic acid composite material. The composite material was subject to injection molding followed by mechanical property tests. The results were shown in Table 4.

For the polylactic acid composite material, the mass percent of hydroxyapatite was 30% as measured by the TGA test, and the stereocomplex crystallization ratio of the polylactic acid composite material was 40% as measured by the DSC test.

Example 6

Tricalcium phosphate of 2 g having a granule size of 200 nm was dispersed in 100 ml of toluene, to which 6 g of caprolactone and 160 μl of stannous octoate were added. The mixture was heated under stirring to 150° C. in the presence of an inert gas, and the reaction was performed for 12 hours. Then, 6 g of glycolide was added to the mixture, and the reaction was performed for 12 hours. Thereafter, 3 g of caprolactone was added and the reaction was performed for 6 hours, thereby obtaining a tricalcium phosphate-rubbery layer polymer (tricalcium phosphate-rubbery layer).

Then, 5 g of D-lactide was added to the reaction system, and the reaction was performed for 3 hours. Then, 2 g of glycolide was added, and the reaction was performed for 2 hours. Then, 3 g of D-lactide was added, and the reaction was performed for 4 hours, to obtain core-shell structures composed of tricalcium phosphate, a rubbery layer and poly(D-lactide-co-glycolide) block copolymer.

The products from the two above stages were separately dissolved in chloroform, and free molecular chains not attached to tricalcium phosphate were removed by centrifugation, to obtain a tricalcium phosphate-rubbery layer polymer (tricalcium phosphate-rubbery layer) and core-shell structures, respectively. The removed free molecular chains, i.e., the rubbery molecular chains and the rubbery layer-poly(D-polylactide-co-glycolide) block copolymer molecular chains (rubbery layer-poly(D-lactide-co-glycolide) block copolymer) were subject to DSC tests to detect the glass transition temperatures. The results were shown in Table 3.

The polylactic acid matrix was prepared by the following method. In specific, 25 mg of ethylene glycol, 160 μl of stannous octoate, and 45 g of L-lactide were heated under stirring to 180° C., and reacted for 36 hours. The mixture was then added with 5 g of caprolactone, and continued to react for 12 hours. The resultant products were purified by a chloroform-methanol system, wherein the obtained polylactic acid matrix was a poly(L-lactide-co-caprolactone) block copolymer (Mn=105,000, glass transition temperature of 50° C.).

The core-shell structures and the polylactic acid matrix were blended in chloroform and precipitated in methanol to obtain a polylactic acid composite material. The composite material was subject to injection molding followed by mechanical property tests. The results were shown in Table 4.

For the polylactic acid composite material, the mass percent of hydroxyapatite was 15% as measured by the TGA test, and the stereocomplex crystallization ratio of the polylactic acid composite material was 20% as measured by the DSC test.

Comparative Example 4

Hydroxyapatite of 2 g having a granule size of 5 nm was dispersed in 100 ml of toluene, to which 9 g of caprolactone, 6 g of L-lactide and 160 μl of stannous octoate were added. The mixture was heated under stirring to 80° C. in the presence of an inert gas, and the reaction was performed for 2 hours. Then, 5 g of L-lactide was added, and the reaction was continued for 2 hours.

The products from the above two stages were separately dissolved in chloroform, and free molecular chains not attached to hydroxyapatite were removed by centrifugation to obtain a hydroxyapatite-rubbery layer polymer (hydroxyapatite-rubbery layer), and a core-shell structure composed of hydroxyapatite, a rubbery layer and poly(L-lactic acid), respectively. The removed free molecular chains, i.e., the rubbery layer molecular chain and the rubber layer-poly(L-lactic acid) polymer molecular chains were subject to DSC tests to detect the glass transition temperatures. The results were shown in Table 3.

The core-shell structures and the poly(L-lactic acid) (Mn=120,000, glass transition temperature of 55° C.) were finally blended in chloroform and precipitated in methanol to obtain a polylactic acid composite material. The composite material was subject to injection molding and mechanical property test, and the results were shown in Table 4.

The mass percent of hydroxyapatite in the polylactic acid composite material was determined by the TGA test to be 1%.

Comparative Example 5

Hydroxyapatite of 2 g having a granule size of 5 nm was dispersed in 100 ml of toluene, to which 5 g of D-lactide and 160 μl of stannous octoate were then added. The mixture was heated under stirring to 80° C. in the presence of an inert gas, and the reaction was performed for 2 hours.

The product was dissolved in chloroform, and free molecular chains not attached to hydroxyapatite were removed by centrifugation, to obtain a hydroxyapatite-poly-D-lactide polymer (hydroxyapatite-poly-D-lactide). The removed free molecular chains, i.e., the poly-D-lactide molecular chains were subject to the DSC (Differential Scanning calorimetry) test to detect the glass transition temperature of the material. The results were shown in Table 1.

The hydroxyapatite-poly-D-lactide polymer (hydroxyapatite-poly-D-lactide) and the poly-L-lactide (Mn=120,000, glass transition temperature of 55° C.) were finally blended in chloroform and precipitated in methanol to obtain a polylactic acid composite material. The composite material was subject to injection molding and mechanical property test, and the results were shown in Table 2.

The mass percent of hydroxyapatite in the polylactic acid composite material was determined by the TGA (Thermogravimetric Analysis) test to be 1%.

Comparative Example 6

The poly-L-lactide (Mn=120,000, glass transition temperature of 55° C.) was subject to injection molding, and the mechanical properties were shown in Table 4.

As shown in Table 3 and Table 4, it can be seen from Example 4 in comparison to Comparative Example 6 that the interface design as employed in the present disclosure simultaneously and effectively improved the mechanical strength (Young's modulus and tensile strength) and the toughness (elongation at break) of the polylactic acid composite material.

As can be seen from Example 4 and Comparative Example 5 that the rubbery layer functions as a buffer between the substrate granules and the polylactic acid matrix, which improved the toughness of the polylactic acid composite material.

In Comparative Example 4, there is no strong stereocomplex interfacial force between the core-shell structures and the polylactic acid matrix. Therefore, it can be seen from Example 4 and Comparative Example 4 that the stereocomplex force in the absorbable polylactic acid composite material of the present disclosure played an important role in improving the mechanical properties of the material.

Although the present disclosure has been described in detail with reference to the accompanying drawings and embodiments, it should be understood that the above description is not intended to limit the present disclosure in any way. The present disclosure may be modified and changed as needed by those skilled in the art without departing from the spirit and scope of the present disclosure, and these modifications and variations fall within the scope of the present disclosure.

We claim:

1. An absorbable biomedical composite material comprising:
    a polymer matrix having a second glass transition temperature, and
    a plurality of substrate granules comprising hydroxyapatite, wherein each substrate granule is coated with an intermediate layer and distributed in the polymer matrix, the intermediate layer having a first glass transition temperature that is not higher than normal human body temperature,
wherein:
    the second glass transition temperature is higher than the first glass transition temperature;
    the intermediate layer comprises a random copolymer of lactide and caprolactone;
    the polymer matrix comprises a homopolymer of lactide;
    the absorbable biomedical composite material comprises 1 wt % to 10 wt % of the intermediate layer;
    each of the substrate granules is covalently bonded to the intermediate layer; and
    the intermediate layer and the polymer matrix do not form a stereocomplex.

2. The biomedical composite material according to claim 1, comprising 1 wt % to 10 wt % of the substrate granules.

3. The biomedical composite material according to claim 1, wherein the polymer matrix is formed on the intermediate layer in an in situ polymerization manner.

* * * * *